United States Patent [19]
Haga et al.

[11] Patent Number: 5,737,074
[45] Date of Patent: Apr. 7, 1998

[54] SURFACE INSPECTION METHOD AND APPARATUS

[75] Inventors: Kazumi Haga; Motoshi Sakai, both of Komae, Japan

[73] Assignee: New Creation Co., Ltd., Tokyo, Japan

[21] Appl. No.: 760,603

[22] Filed: Dec. 4, 1996

[30] Foreign Application Priority Data

Dec. 5, 1995 [JP] Japan .................................. 7-316511

[51] Int. Cl.$^6$ .................................................. G01N 21/00
[52] U.S. Cl. ........................................... 356/237; 356/371
[58] Field of Search ................................. 356/371, 237, 356/239, 394, 445, 446, 375, 376

[56] References Cited

U.S. PATENT DOCUMENTS

| | | | |
|---|---|---|---|
| 3,484,150 | 12/1969 | Taoka et al. | 356/237 |
| 3,782,827 | 1/1974 | Nisenson et al. | 356/237 |
| 3,815,998 | 6/1974 | Tietze | 356/371 |
| 4,547,073 | 10/1985 | Kugimiya | 356/371 |
| 4,818,108 | 4/1989 | Eppinger | 356/124 |
| 5,461,228 | 10/1995 | Kirkman et al. | 356/240 |

*Primary Examiner*—Hoa Q. Pham
*Attorney, Agent, or Firm*—Evenson, McKeown, Edwards & Lenahan, P.L.L.C.

[57] ABSTRACT

The method comprises the steps of: irradiating an objective region to be measured with an illuminating light in an oblique direction thereto; forming an image of reflected light from the objective region by member of an object-side telecentric optical system or an image-object-side telecentric optical system, which has an optical axis coinciding with an incident direction of the illuminating light to the objective region and has a object-side angular aperture against a point on the objective region, which is set at a predetermined angle; picking up the formed image to collect luminance data of respective points in the objective region; and processing the luminance data to recognize bright and dark portions and thereby determining the presence or absence of an irregular portion and a shape of the irregular portion, in the objective region. The method enables measurement of the presence or absence of irregularity and the shape of the irregularity in a wide surface region with a high accuracy and in a single operation by using an apparatus having relatively simple construction.

20 Claims, 14 Drawing Sheets

FORMED IMAGE

INCIDENCE

OBJECT-SIDE ANGULAR APERTURE

REFLECTION

NO REFLECTION INCLUDED IN
OBJECT-SIDE ANGULAR APERTURE

ILLUMINATION ANGULAR APERTURE

INCIDENCE

REFERENCE PLANE

REFLECTION

REFLECTION PARTIALLY INCLUDED
IN OBJECT-SIDE ANGULAR APERTURE

SURFACE INSPECTION METHOD AND APPARATUS

BACKGROUND OF THE INVENTION

1. Field of the Invention

This invention relates to a surface inspection method and an apparatus for carrying out the method, for measuring the shape or the state of objective regions to be measured, more particularly a surface inspection method and an apparatus suitable for inspection of surface characteristics of specific objective regions to be measured.

2. Description of Related Art

Measurement of the shape or the state of a surface of an object is carried out for an instrumentation of the object's characters, a decision whether the quality of the object is good or not as a product, and the like. In particular, measurement of the shape or the state of the surface of the object is often used for measuring the irregularity of a surface of an object having a plate-like shape.

FIG. 14 shows a typical example of a measuring apparatus for measuring the irregularity of the surface of the object having a plate-like shape. As shown in this Figure, the measuring apparatus is provided with (a) a light source 910 for generating substantially parallel light beams, (b) a half mirror 920 for accepting the light beams output from the light source 910 and for outputting these light beams toward a specific measurement objective region on the object 990 to be measured, (c) an image formation system 930 for receiving the reflected light from the measurement objective region of the object 990 and for forming an image thereof, (d) an image pickup part 940 having a light receiving surface 941 at the image formation surface of the image formation system 930, (e) an image information processor 950 for collecting the luminance data output from the image pickup part 940 and for image processing the collected data.

By using the above described measuring apparatus, measurement of the shape or the like of the objective region is carried out as follows:

Substantially a parallel light beam outputs from the light source 910 are irradiated through the half mirror 920 onto measurement objective regions of the object 990 to be measured. Light beams reflected from the measurement objective region forms an image through the image formation system 930, and the formed image is picked up by the image pickup part 940. The picked up image results are output from the image pickup part 940 and are collected by the image information processor 950. The processor 950 reconstructs the image of the measurement objective region by processing the collected luminance data. By inspection of the obtained image of the measured objective region, the presence or absence of irregularity or the position of the irregularity is measured through fading (unsharp) portions in the image.

Conventionally, since an object shape measurement has been carried out as described above, an approximate shape of the irregular portion could be recognized. However, when the irregular portion such as a concave or a convex, has a gentle slope such as a circular cone or the like, the unsharpness of the image gradually proceeds from the peripheral portion to the central portion thereof, so that the outer rim of the irregular portion could not be discriminated and a precise measurement for the shape of the irregular portion could not be performed.

Accordingly, in order to precisely measure the shape of the irregular portion, use of a large scale, complicated and expensive apparatus such as a scanning electron microscope has been required.

SUMMARY OF THE INVENTION

The present invention was developed in view of the above-described problems. An object of the present invention is to provide an improved surface inspection method which enables measurement of the presence or absence of irregularity and the shape of the irregularity in a wide surface region with a high accuracy and in a single operation by using an apparatus having relatively simple construction. Another object of the present invention is to provide an improved surface inspection apparatus having a simple construction for suitably carrying out the surface inspection method according to the invention.

In accordance with one aspect of the present invention, the surface inspection method for inspecting a surface condition of an objective region to be measured by irradiating the objective region with an illuminating light of a parallel beam, comprising the steps of: irradiating an objective region to be measured with an illuminating light in an oblique direction thereto; forming an image of reflected light from the objective region by member of an object-side telecentric optical system or an image-object-side telecentric optical system, which has an optical axis coinciding with an incident direction of the illuminating light to the objective region and has a object-side angular aperture against a point on the objective region, which is set at a predetermined angle; picking up the formed image to collect luminance data of respective points in the objective region; and processing the luminance data to recognize bright and dark portions and thereby determining the presence or absence of an irregular portion and a shape of the irregular portion, in the objective region.

In the specification, the term "a parallel light beam" member not only a perfect parallel light beam but also includes a parallel light beam formed from a pseudo-point light source.

In accordance with another aspect of the present invention, the surface inspection method for inspecting a surface condition of an objective region to be measured by irradiating the objective region with an illuminating light of a parallel beam, comprising the steps of: inclining an object to be measured and irradiating an objective region to be measured with an illuminating light in an oblique direction thereto; forming an image of reflected light from the objective region with respective luminances corresponding to incident angles at respective points in the objective region, by member of an object-side telecentric optical system or an image-object-side telecentric optical system, which has an optical axis coinciding with an incident direction of the illuminating light to the objective region and has a object-side angular aperture against a point on the objective region, which is set at a predetermined angle; picking up the formed image to collect luminance data of respective points in the objective region; and processing the luminance data to determine an inclination distribution of the objective region on the basis of linear differential results of the luminance data and to determine the presence or absence of an irregular portion and a shape of the irregular portion, in the objective region, on the basis of the difference between a regression curve obtained from an integral data of the luminance data and the integral data.

In accordance with another aspect of the present invention, the surface inspection apparatus for inspecting a surface condition of an objective region to be measured by irradiating the objective region, comprising: a light irradiating member for irradiating the objective region with an illuminating light of a parallel beam thereto; an angle setting member for inclining an object to be measured to irradiate an objective region to be measured with the illuminating light in an oblique direction thereto; an object-side telecentric optical system or an image-object-side telecentric optical system, for forming an image of reflected light from the objective region, which has an optical axis coinciding with an incident direction of the illuminating light to the objective region and has a object-side angular aperture against a point on the objective region, which is set at a predetermined angle; a pick-up part for picking up the formed image to collect luminance data of respective points in the objective region; and a processing part for processing the luminance data to recognize bright and dark portions and thereby determining the presence or absence of an irregular portion and a shape of the irregular portion, in the objective region.

In accordance with another aspect of the present invention, the surface inspection apparatus for inspecting a shape of an irregular portion in an objective region to be measured by irradiating the objective region, comprising: a light irradiating member for irradiating the objective region with an illuminating light of a parallel beam; an angle setting member for inclining an object to be measured to irradiate an objective region to be measured with the illuminating light in an oblique direction thereto; an object-side telecentric optical system or an image-object-side telecentric optical system, for forming an image of reflected light from the objective region with respective luminances corresponding to incident angles at respective points in the objective region, which has an optical axis coinciding with an incident direction of the illuminating light to the objective region and has a object-side angular aperture against a point on the objective region, which is set at a predetermined angle; a pick-up part for picking up the formed image to collect luminance data of respective points in the objective region; and a processing part for processing the luminance data to determine an inclination distribution of the objective region on the basis of linear differential results of the luminance data and to determine the presence or absence of an irregular portion and a shape of the irregular portion, in the objective region, on the basis of the difference between a regression curve obtained from an integral data of the luminance data and the integral data.

Preferably, the surface inspection apparatus further comprises an angular aperture changing member for changing the object-side angular aperture. The light irradiating member may comprise a light source and an aperture stop, and the apparatus further comprises an aperture diameter changing member for changing an aperture diameter of the aperture stop correspondingly to a change of the object-side angular aperture.

Preferably, in the processing part, a first luminance data of respective points in the objective region when the object to be measured is inclined at a predetermined angle in one direction with respect to an axis in a reference plane which is perpendicular to the incident direction of the illuminating light and a second luminance data of respective points in the objective region when the object to be measured is inclined at the same angle as the above in the other direction with respect to the axis are summed together, and about ½ of the maximum value of the summed value is used as a value for medium gradation and at least one of the first and second luminance data is used as a processing objective luminance data.

In the processing part, both a luminance data when the object to be measured is inclined with respect to one axis in a reference plane which is perpendicular to the incident direction of the illuminating light and a luminance data when the object to be measured is inclined with respect to another axis in the reference plane, which is perpendicular to the one axis, may be used as processing objective luminance data, and these two processing objective luminance data maybe composited to determine the presence or absence of an irregular portion and a shape of the irregular portion, on the object to be measured.

BRIEF DESCRIPTION OF THE DRAWINGS

The present invention will become more fully understood from the detailed description given hereinbelow and the accompanying drawings which are given byway of illustration only, and thus do not limit the present invention, and wherein.

DESCRIPTION OF THE PREFERRED EMBODIMENT

Figure 1:
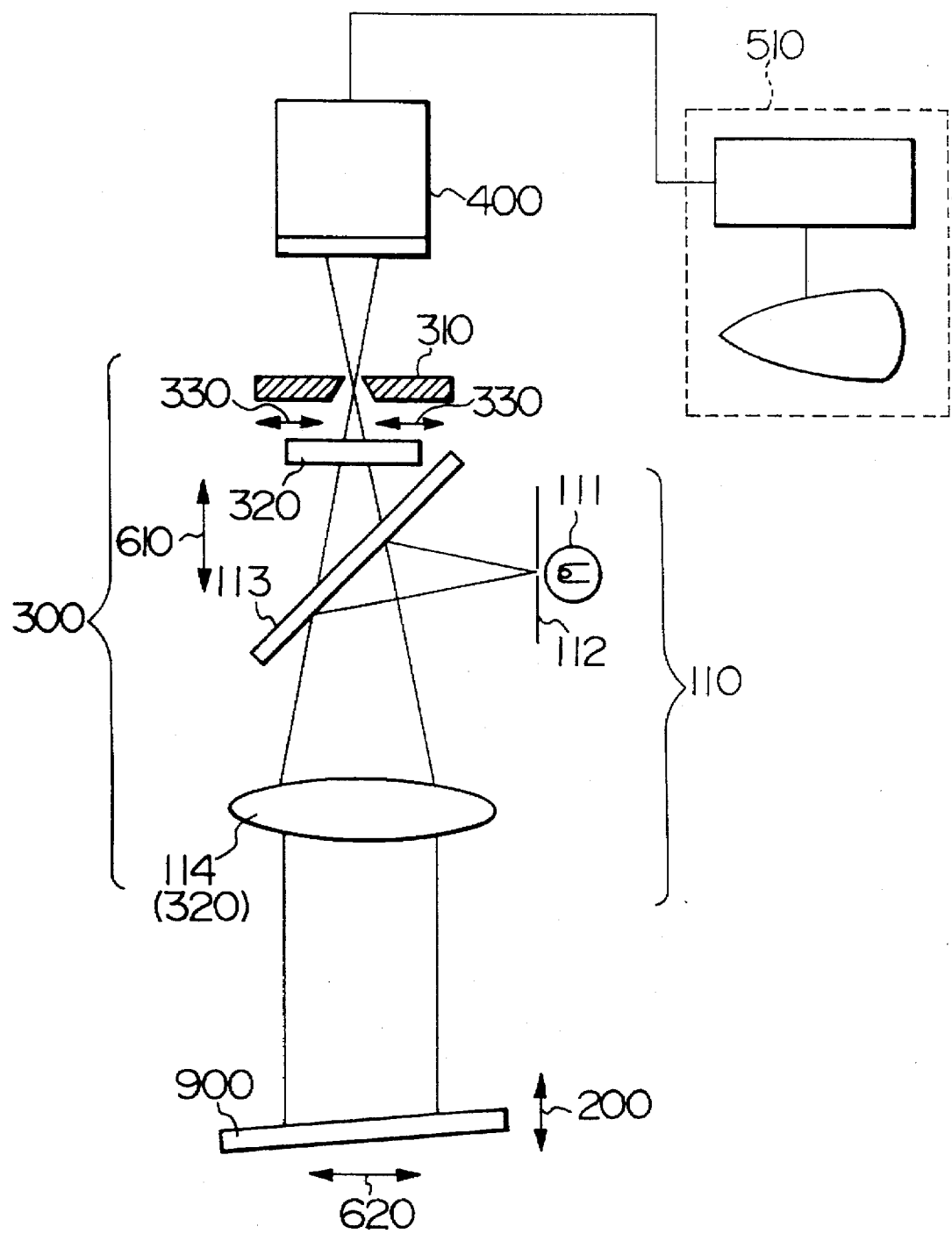
FIG. 1 is a schematic view showing the construction of a surface inspection apparatus according to the first embodiment of the present invention.

Hereinafter, the surface inspection method and the surface inspection apparatus according to embodiments of the present invention will be explained with reference to the drawings. In the drawings showing a plurality of embodiments, the same structural members, elements or the like are designated with the same reference numerals, and overlapping explanations are avoided.

FIG. 1 shows a construction of a surface inspection apparatus according to the first embodiment of the present invention. As shown in FIG. 1, this apparatus is provided with a light irradiation member 110 for irradiating an objective region to be measured with an illuminating light of a parallel light beam, an angle setting member 200 which enables inclination of the objective region to be measured so as to irradiate the objective region with an illuminating light from an oblique direction with respect to the surface of the objective region, an object-side telecentric optical system 300 having an optical axis coinciding with the incident direction of the illuminating light onto the objective region to be measured and having a predetermined object-side angular aperture with respect to a point on the objective region so as to form an image of reflected light issued from the objective region, an image pickup part 400 for picking up the formed image to collect luminance data of respective pixels (respective points on objective region to be measured), and a processing part 510 for determining the presence or absence of an irregular portion in the objective region to be measured, and the shape of the irregular portion, on the basis of the luminance data.

In this construction, the light irradiating member 110 comprises a light source 111, an aperture 112, a half mirror 113 and a collimating lens 114. The collimating lens 114 constitutes also a part of the image formation system. Further the object-side telecentricoptical system 300 is provided with (1) an image formation lens system 320 including the collimating lens 114, (2) a light limiting member 310 such as an aperture stop, an aperture or the like, located at the position of a stop of the object-side telecentric optical system 300, and (3) an angular aperture changing member 330 for changing the aperture diameter of the light limiting member 310 to change the object-side angular aperture of the object-side telecentric optical system 300.

In the surface inspection apparatus according to the first embodiment, when the illuminating light is a substantially perfectly parallel light beam and the aperture diameter of the light limiting member 310 is very small, the image formed by the object-side telecentric optical system 300 becomes an image of two gradations of brightness and darkness which depend on the incident angle at respective points in the measurement objective region.

Figure 2:
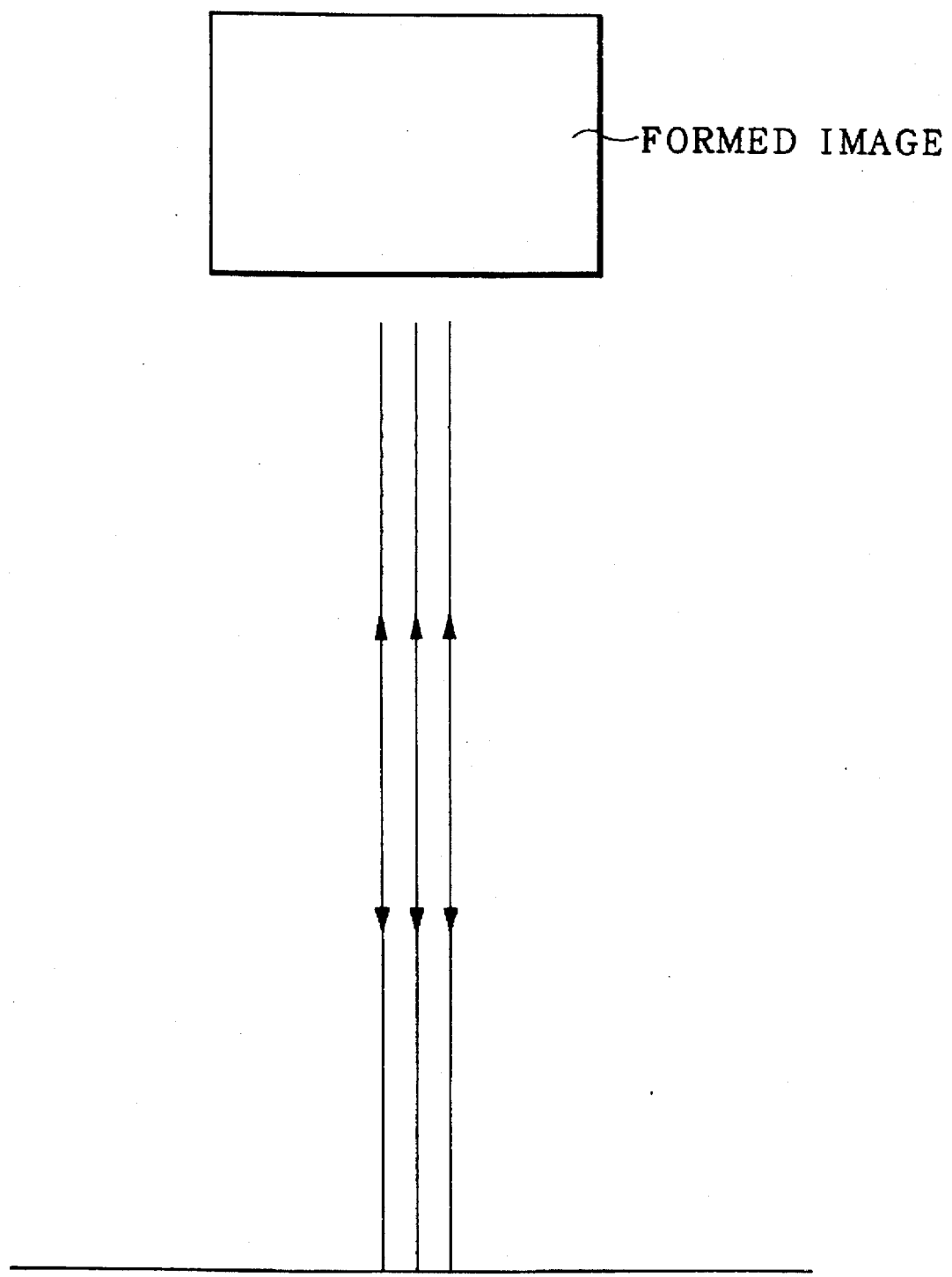
FIG. 2 is an explanation view of image formation operation of the surface inspection apparatus according to the first embodiment of the present invention.
Figure 3:
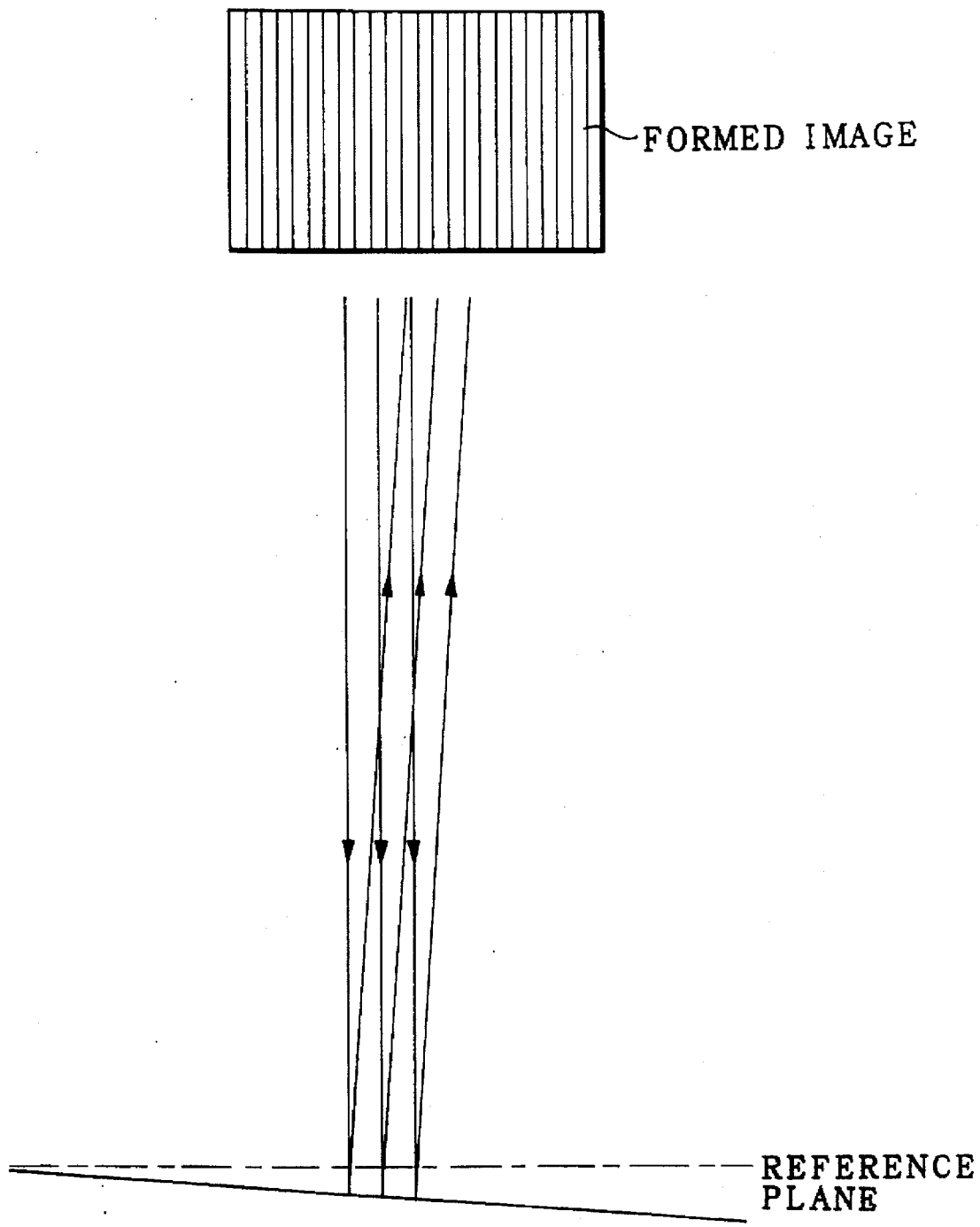
FIG. 3 is an explanation view of image formation operation of the surface inspection apparatus according to the first embodiment of the present invention.

More specifically, as shown in FIG. 2, when an illuminating light is irradiated on an object 900 to be measured having an even measurement objective region from the normal direction thereto (that is, with an incident angle=0), the illuminating light is reflected in normal direction with respect to the measurement object region (which is the same direction as the incident, that is, with a reflecting angle=0), in accordance with the law of reflection. In the surface inspection apparatus according to the embodiment, the reflected light enters into the aperture of the light limiting member 310 of the object-side telecentric optical system 300 and arrives at the image pickup part 400. As a result, the image formed by the object-side telecentric optical system 300 has a luminance of 100%. On the other hand, when the measurement objective region is inclined with respect to the surface (a reference surface) normal to the incident direction, the illuminating light is reflected out of the normal direction (incident direction) with respect to the measurement objective region. Therefore, this reflected light does not enter into the aperture of the light limiting member 310 of the object-side telecentric optical system 300, so that it does not reach the image pickup part 400. As a result, the image formed by the object-side telecentric optical system 300 becomes an image having a luminance of 0%.

As described above, in the surface inspection apparatus according to the embodiment, only when an illuminating light is irradiated to a point in the measurement objective region from the normal direction (that is, with an incident angle=0), the image of the point becomes a bright point having a luminescent of 100%, and another point (for example, a point on a slope surface of a concave) forms a dark image having a luminance of 0%.

The apparatus according to the first embodiment can inspect the surface condition in the measurement objective region of the object 900 to be measured by utilizing such a property as described above.

Figure 4:
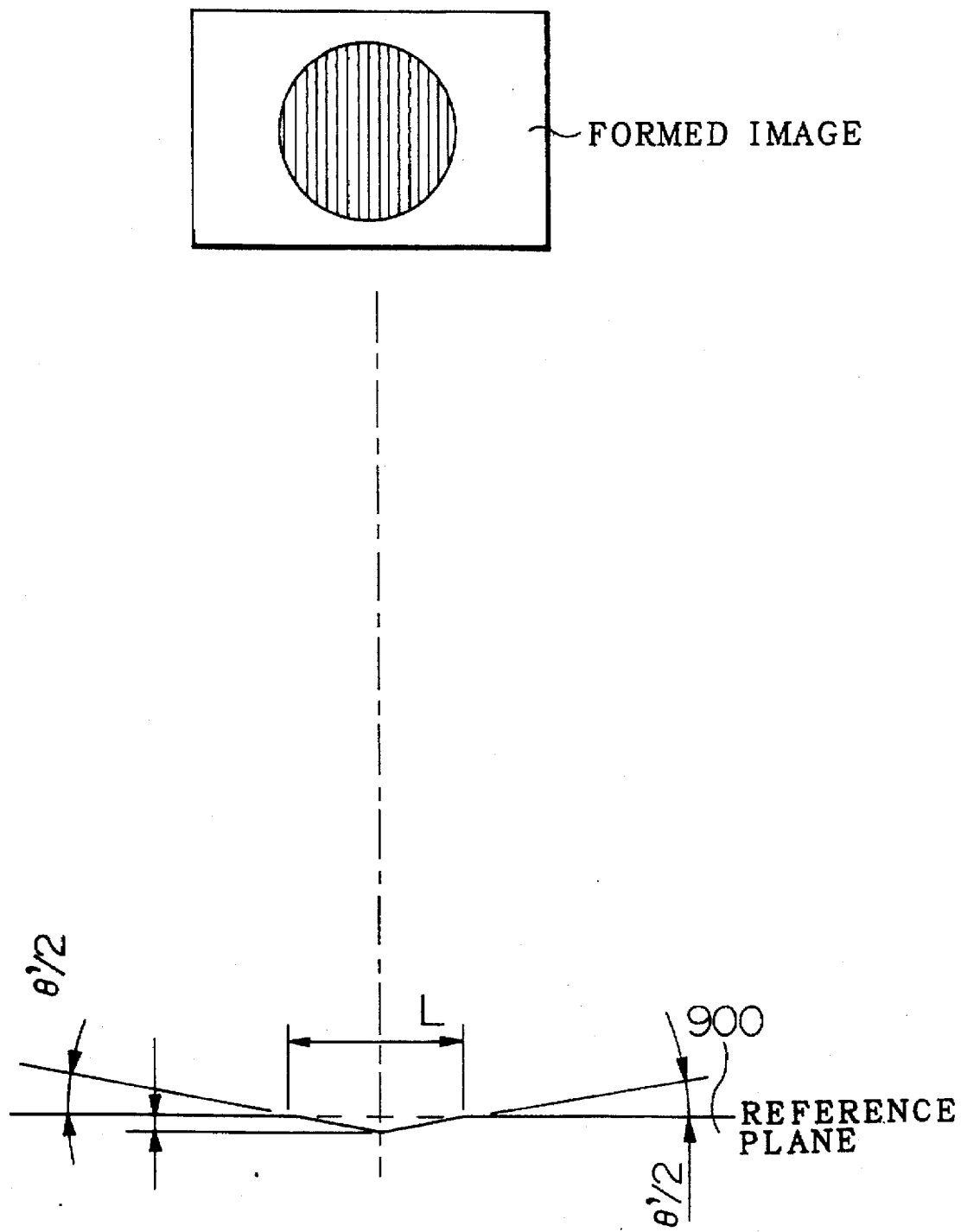
FIG. 4 is an explanation view of image formation operation of the surface inspection apparatus according to the first embodiment of the present invention.

It is now assumed that the object-side angular aperture $\theta$ of the object-side telecentric optical system 300 is substantially 0 (zero), and that a conical concave is found in the measurement objective region (substantially a flat surface) of the object 900 to be measured, as shown in FIG. 4, and that there is a relationship between the inclination angle of the sloping surface of the concave=$\theta'/2$, the diameter=L, and depth=d, as shown in the following equation:

$$d = (L/2) \tan(\theta'/2).$$

In this case, when an illuminating light is irradiated from the normal direction to the measurement object 900, the illuminating light to the recess is reflected out of the incident direction in the recess, so that the reflected light does not enter the aperture of the light limiting member 310, and it does not reach the image pickup part 400. As a result, the image of the concave formed by the object-side telecentric optical system 300 comes to have a luminance of 0%, which is shown in FIG. 4.

Figure 5:
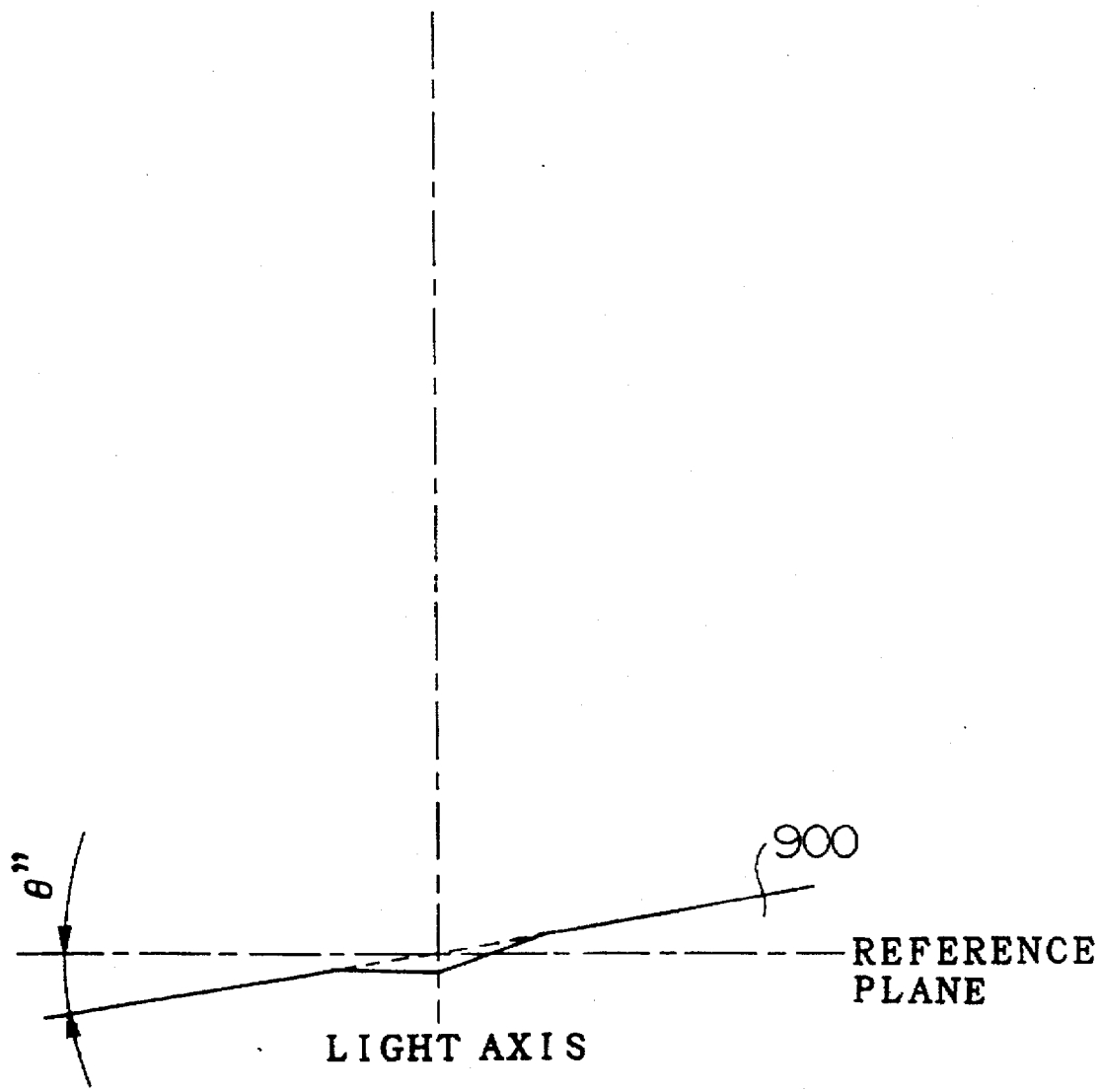
FIG. 5 is an explanation view of image formation operation of the surface inspection apparatus according to the first embodiment of the present invention.

When assuming then that the measurement objective region is inclined at an angle of $\theta''$ from the state shown in FIG. 4, the inclination of one side slope of the concave with respect to a plane (that is, the reference plane) normal to incident direction is now $((\theta'/2)-\theta'')$, and the inclination of the other side slope of the recess with respect to the reference plane is now $((\theta'/2)+\theta'')$, as shown in FIG. 5. In this case, when the inclination $((\theta'/2)-\theta'')$ is set to be zero, that is, when $(\theta'/2)=\theta''$, the reflected light from the slope having the inclination $((\theta'/2)-\theta'')$ does enter the aperture of the light limiting member 310 of the object-side telecentric optical system 300, while the reflected light from the portion other than the slope having the inclination $((\theta'/2)-\theta'')$ does not enter the aperture of the light limiting member 310. Accordingly, an image comprising a bright region having a luminance of 100% for the slope of the inclination $((\theta'/2)-\theta'')$ and a dark region having a luminance of 0% for the other portion, is formed on an image pickup surface of the image pickup part 400. This means that irregular portions having various sloping angles can be detected by changing the inclination angle $\theta''$. That is, it is possible to detect various irregular portions by variously changing the inclination of the measurement objective regions.

As described above, it is possible to measure the presence or absence of irregularity and the shape of the irregularity, i.e., concave portions or convex portions, by adjusting the inclination angle $\theta''$ of the illuminating light with respect to the objective region to be measured, by means of the angle setting member 200. Further, by changing the object-side angular aperture of the light limiting member 310 by means of the angular aperture changing member 330, it is possible to change the detection sensitivity for measuring the irregular portions.

Figure 6:
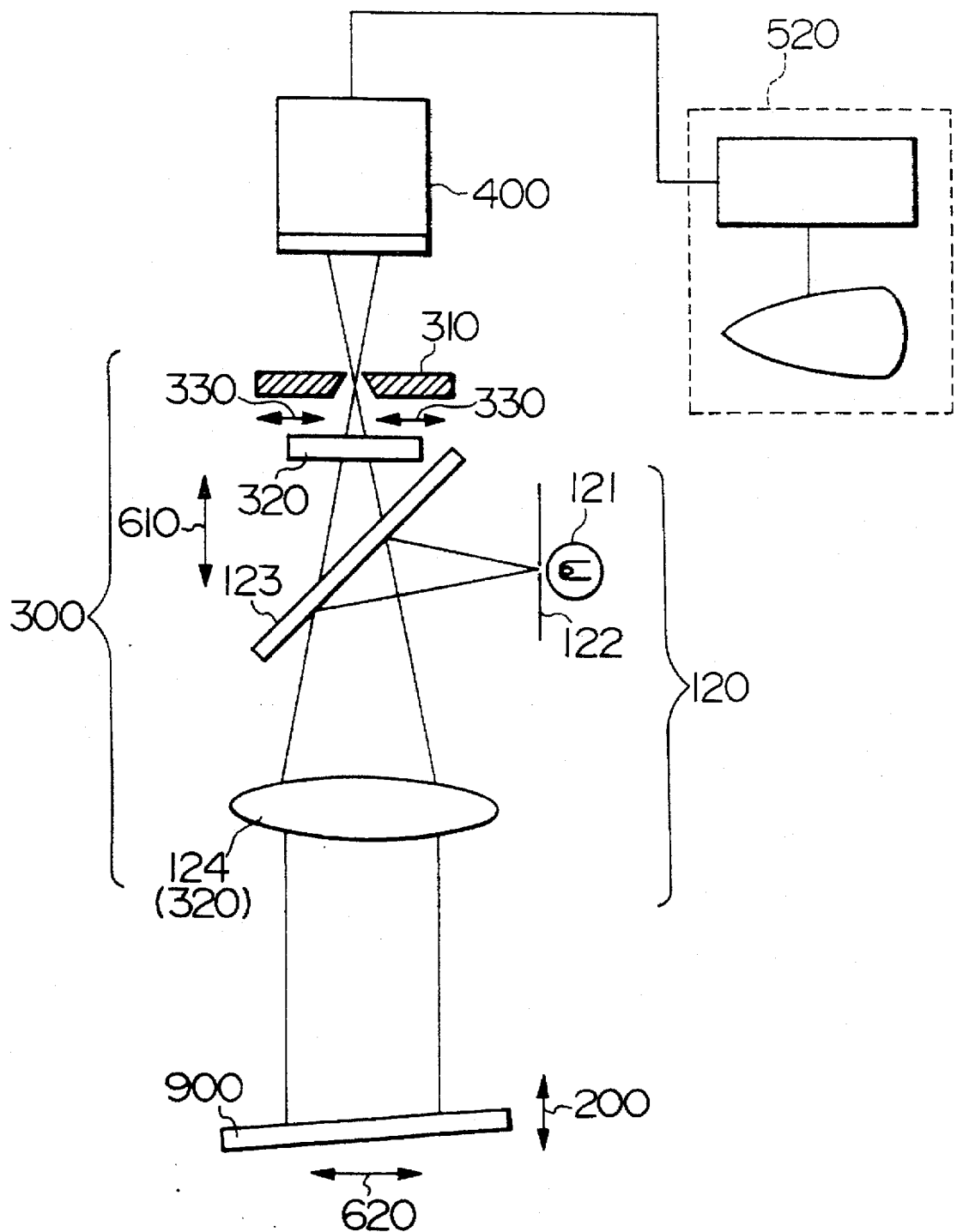
FIG. 6 is a schematic view showing the construction of a surface inspection apparatus according to the second embodiment of the present invention.

Next, the surface inspection apparatus according to the second embodiment of the present invention will be explained. In FIG. 6 showing the construction of a surface inspection apparatus according to the second embodiment, the apparatus is provided with a light irradiation member 120 for irradiating a measurement objective region with an illuminating light of a parallel beam which is generated by using a pseudo point light source, an angle setting member 200 for inclining an object to be measured 900 to irradiate the objective region to be measured with the illuminating light in an oblique direction thereto; an object-side telecentric optical system 300 for forming an image of reflected light from the objective region with respective luminances corresponding to incident angles at respective points in the objective region, which has an optical axis coinciding with the incident direction of the illuminating light to the objective region and has a predetermined object-side angular aperture against a point on the objective region, which is set at a predetermined angle; a pick-up part 400 for picking up the formed image to collect luminance data at every picture element (respective points in the objective region); and a processing part 520 for processing the luminance data to determine the inclination distribution of the objective region in the inclination direction of the object to be measured, on the basis of linear differential results of the luminance data and to determine the presence or absence of an irregular portion and a shape of the irregular portion, in the objective region, on the basis of the difference between a regression curve obtained from an integral data of the luminance data and the integral data.

In this construction, the light irradiation member 120 comprises a light source 121, an aperture 122, a half mirror 123, and a collimating lens 124. The collimating lens 124 constitutes also a part of the image formation system. Further the object-side telecentric optical system 300 is provided with (1) an image formation lens system 320 including the collimating lens 124, (2) an aperture stop (a light limiting member) 310 located at the position of a stop of the object-side telecentric optical system 300, and (3) an angular aperture changing member 330 for changing the aperture diameter of the light limiting member 310 to change the object-side angular aperture of the object-side telecentric optical system 300, like the first embodiment.

The surface inspection apparatus according to the second embodiment has a construction which enables inspection of the surface characteristics of the measurement objective region of the object 900 to be measured, by utilizing the fact that the reflection light from respective points on the measurement objective region caused by illumination of illuminating light forms an image through the object-side telecentric optical system 300 with a luminance corresponding to the incident angle (average incident angle) of the illuminating light at the respective points on the measurement objective region.

The reason why the luminance at each point of an image corresponds to the incident angle at the each corresponding point in the measurement objective region is as follows.

Figure 7A:
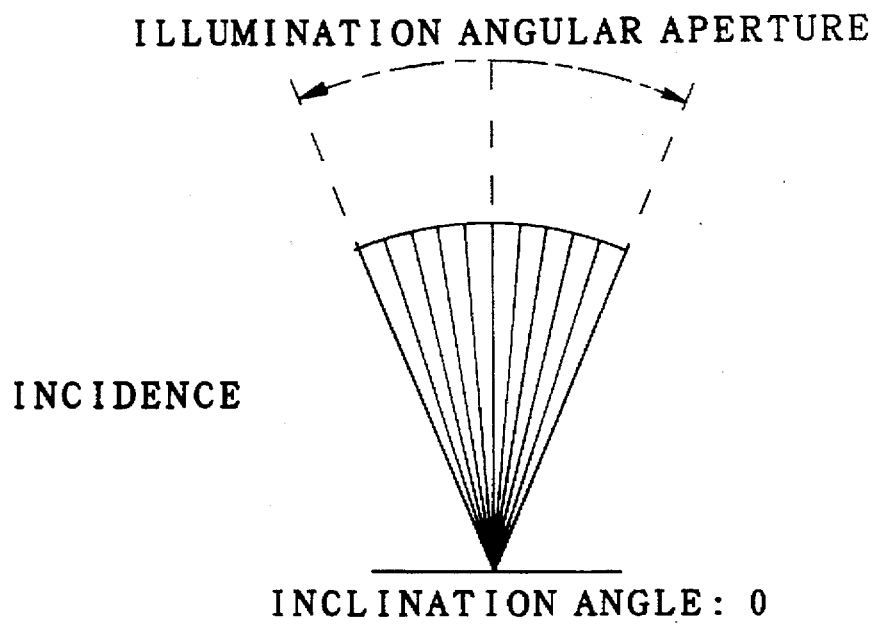
FIGS. 7A and 7B are explanation views of image formation operation of the surface inspection apparatus according to the second embodiment of the present invention.
Figure 7B:
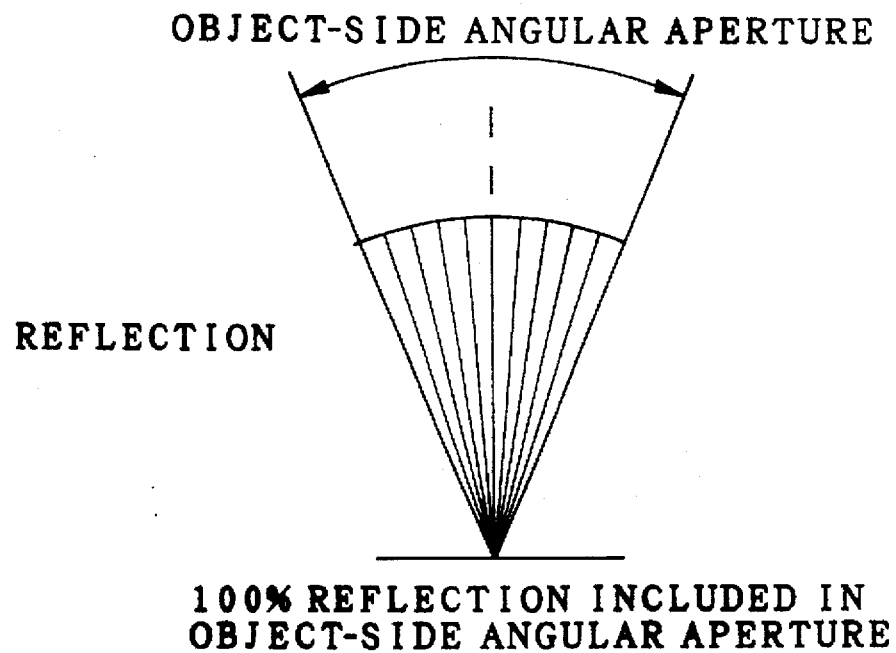

Generally, in order to generate a parallel light beam through the collimating lens 124, making a point light source by using a light source 121 and an aperture or an aperture stop 122 is carried out. However, since the aperture or the aperture stop has a certain degree of size, a perfect point source cannot be obtained. Accordingly, since parallel light beams formed through the collimating lens 124 are not perfect one, light beams having various angle components corresponding to the angular aperture of the aperture or the aperture stop 122 are illuminated onto respective points of the measurement objective region. In other words, the illuminating light is irradiated on the measurement objective region with a certain illumination angular aperture. As a result, even when the measurement objective region has an even surface, reflecting lights which are diffused with a certain angle scope is generated by the surface under the Reflection Law. Assuming now a case where the object-side angular aperture θ is set such that the whole reflecting light beams from a surface parallel to a plane (a reference plane) perpendicular to the incident direction (an average incident direction) of the illuminating light enter just into the aperture stop 310 (that is, in the case of the irradiating angular aperture being equal to the object-side angular aperture θ), the incident light shown in FIG. 7A is reflected on the measurement object region, while the reflected light is diffused in the full scope of θ, as shown in FIG. 7B. In this case, the whole reflecting light are taken into the aperture of the aperture stop 310 to reach the image pick up part 400, so that a bright image with a luminance of 100% is obtained on the surface of this part 400.

Figure 8A:
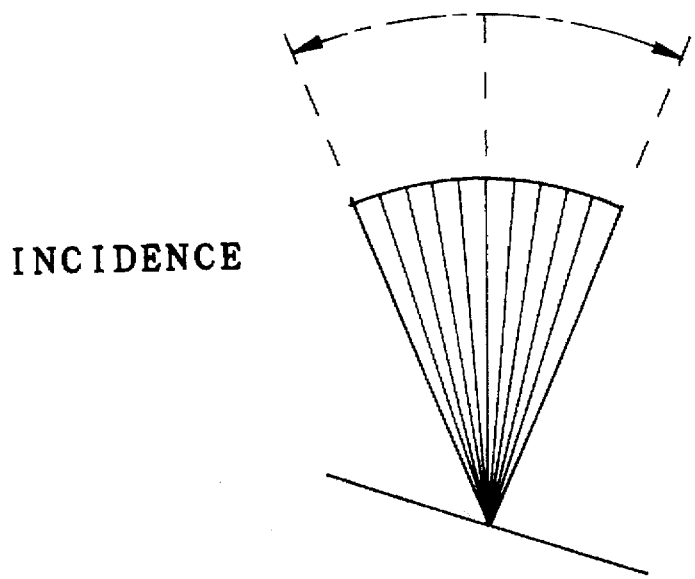
FIGS. 8A and 8B are explanation views of image formation operation of the surface inspection apparatus according to the second embodiment of the present invention.
Figure 8B:
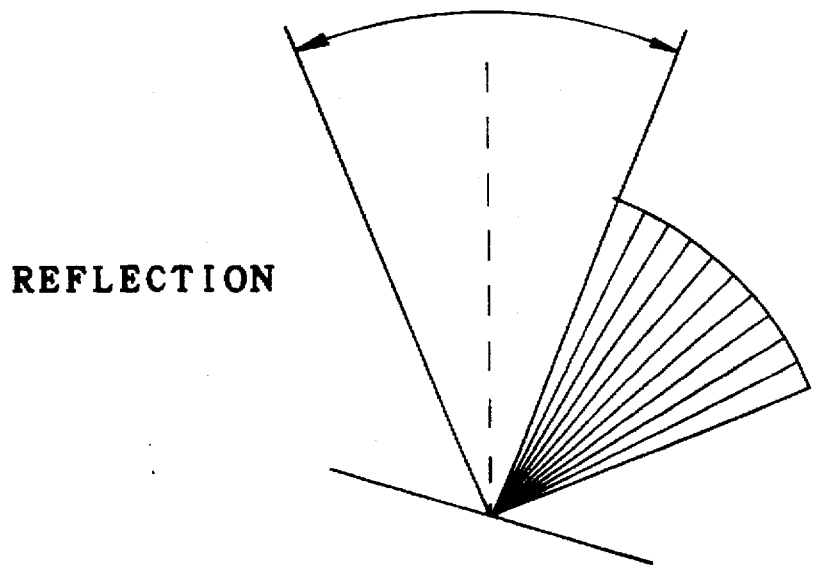
Figure 9A:
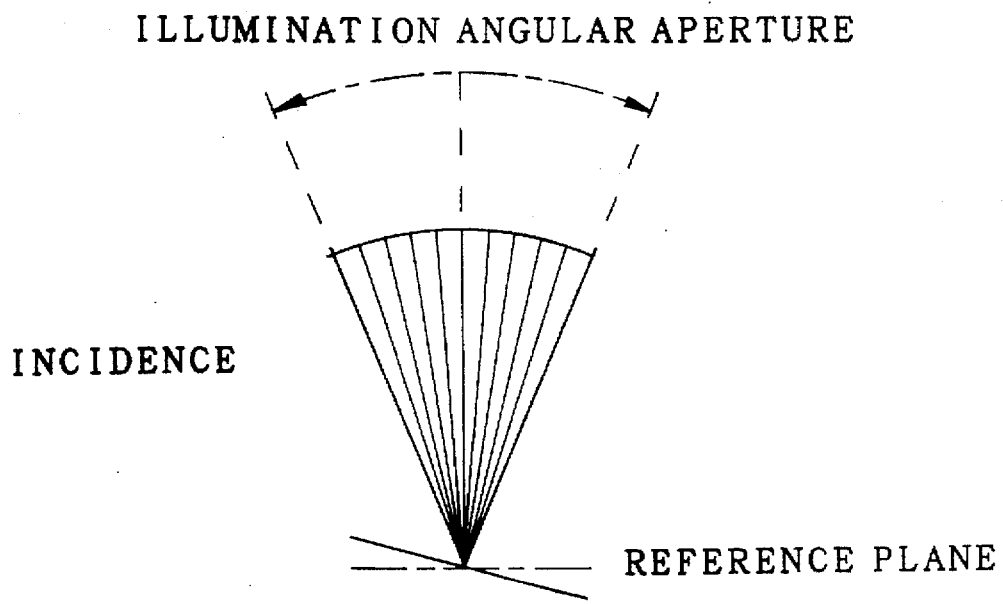
FIGS. 9A and 9B are explanation views of image formation operation of the surface inspection apparatus according to the second embodiment of the present invention.
Figure 9B:
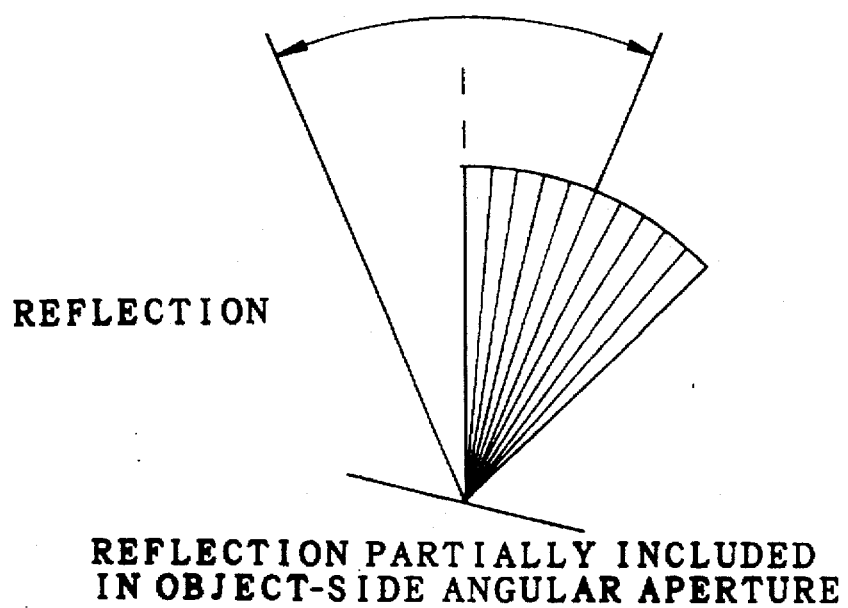

On the other hand, in the case of a surface inclined to the reference plane, the incident illuminating lights shown in FIG. 8A or FIG. 9A are reflected on the surface of the measurement objective region, and the whole or a part of the reflected light are not taken into the aperture of the aperture stop 310, as shown in FIG. 8B or FIG. 9B, so that the obtained image becomes a dark one with a luminance of 0% or one with a luminance corresponding to the quantity of light passing through the aperture of the aperture stop 310.

Next, it is assumed that a conical concave is found in the measurement objective region (substantially flat surface) of the object 900 to be measured, and that there is a relationship between the inclination angle of the sloping surface of the concave=θ'/2, the diameter=L, and depth=d, as shown in the following equation:

$$d = (L/2) \tan(\theta'/2).$$

In cases where the object-side angular angle θ is set so that the whole reflected light beams from a plane parallel to the reference plane enter just the aperture of the aperture stop 310, and the illuminating light is irradiated in the normal direction with respect to measurement objective region, when the inclination angle of the slope (θ'/2) of the concave is larger than (θ/2), the whole reflecting lights from the slope do not pass through the aperture of the aperture stop 310, so that the obtained image of the concave has a luminance of 0%, while the other portions (even portions) have a luminance of 100%.

Figure 10:
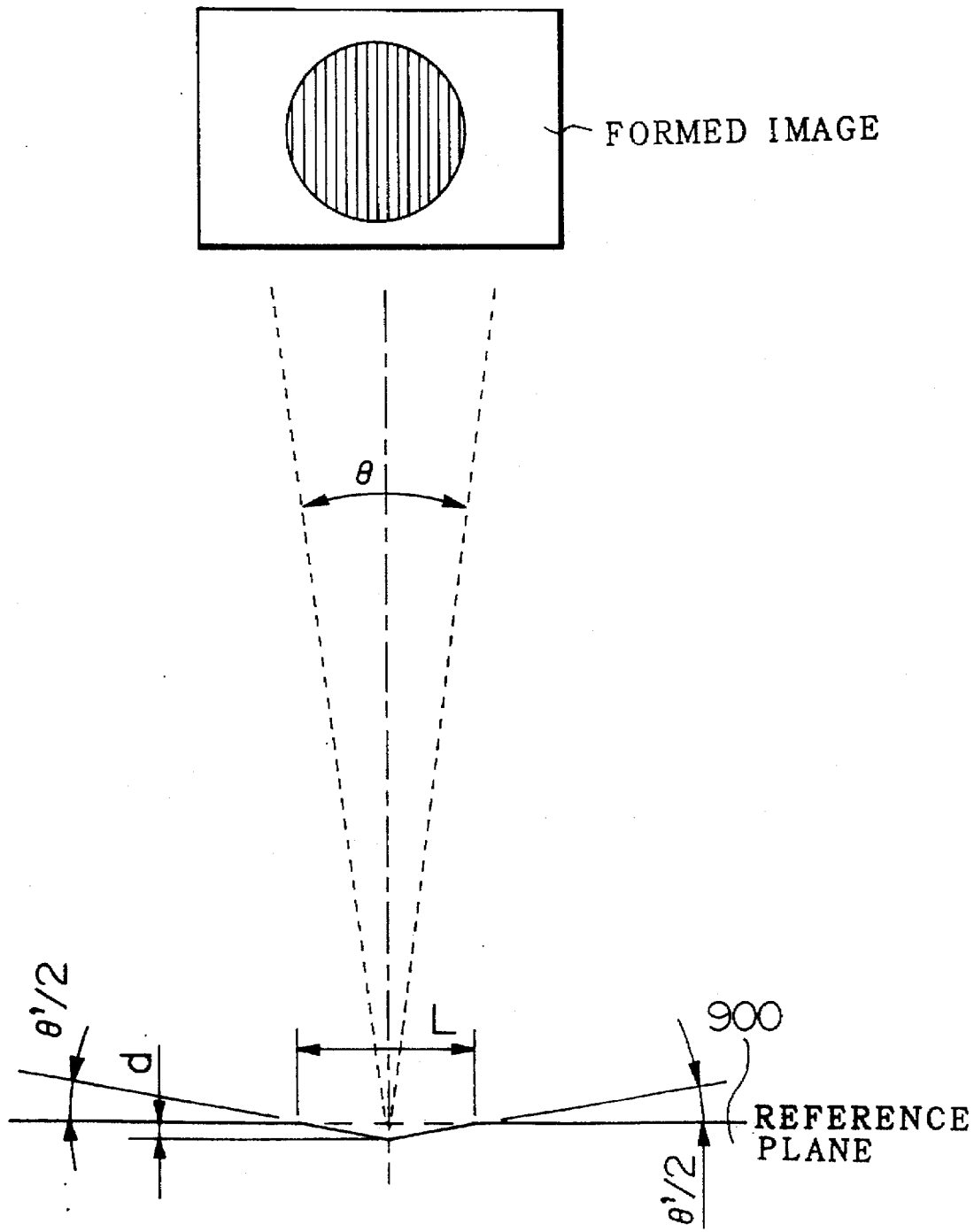
FIG. 10 is an explanation view of image formation operation of the surface inspection apparatus according to the second embodiment of the present invention.
Figure 11:
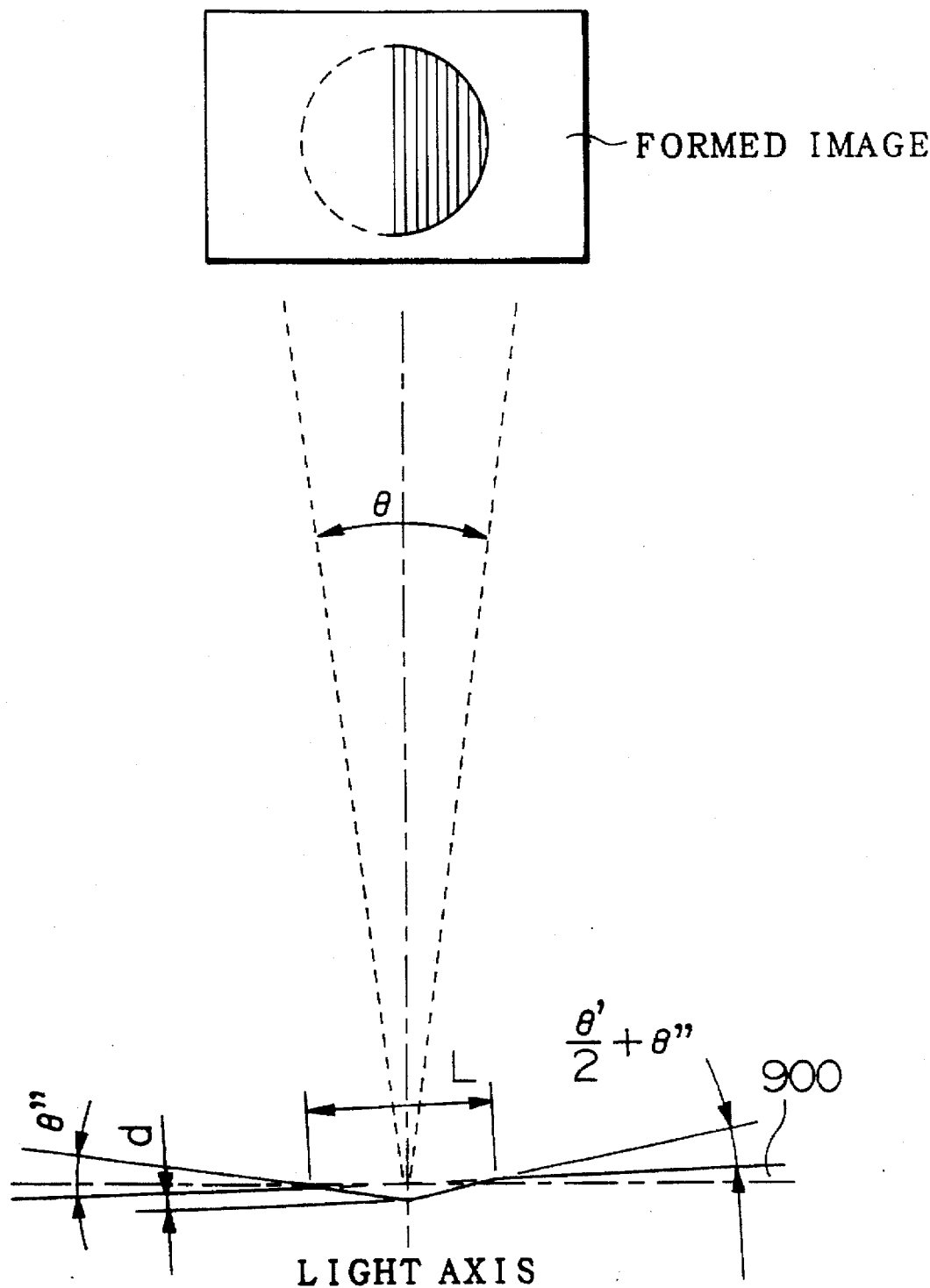
FIG. 11 is an explanation view of image formation operation of the surface inspection apparatus according to the second embodiment of the present invention.
Figure 12A:
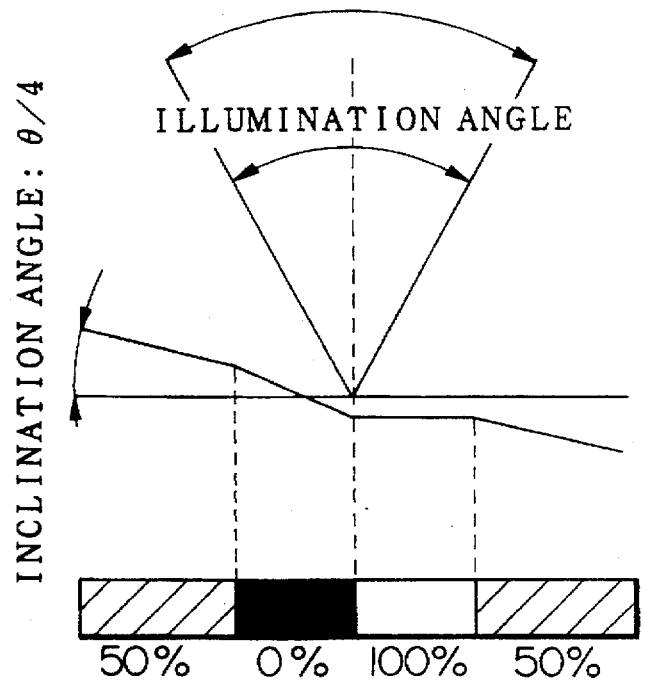
FIGS. 12A and 12B are explanation views of image formation operation of the surface inspection apparatus according to the second embodiment of the present invention.
Figure 12B:
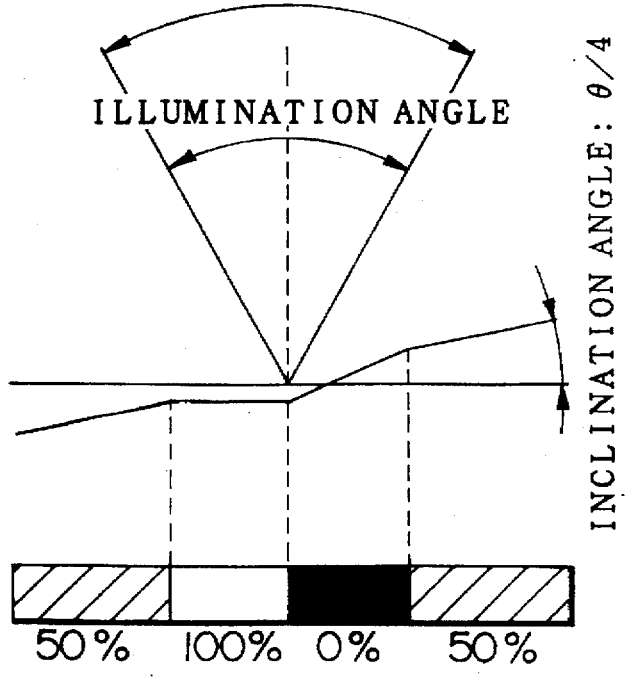

When the measurement objective region is inclined at an angle of θ"(=θ/4) from the state shown in FIG. 10, the inclination of one side slope (surface A) of the concave with respect to the reference plane is now ((θ'/2)−(θ/4)), and the inclination of the other side slope (surface B) with respect to the reference plane is ((θ'/2)+(θ/4)), as shown in FIG. 12A. In this case, when the inclination of the slope (θ'/2) is equal to (θ/4), because the one side slope (surface A) becomes parallel to the reference plane, the whole reflected light from the slope does enter the aperture of the aperture stop 310. As a result, the image of the portion has a luminance of 100%. On the contrary, because the other side slope (surface B) has an inclination of (θ/2) with respect to the reference plane, the whole reflected light from the slope does not enter the aperture of the aperture stop 310. As a result, the image of the slope (surface B) has a luminance of 0%. In this case, because the even portion has an inclination of (θ/4) with respect to the reference plane, only a half of the reflected light from the even portion enter the aperture of the aperture stop 310, the image of the portion has a luminance of about 50%, as shown in FIG. 12B.

On the other hand, in cases where the object-side angular angle θ is set to be twice the spread angle of the reflected lights from the even portion in the measurement objective region (in cases where twice the illumination angle is equal to the object-side angular aperture θ), when the measurement objective region is inclined at an angle of θ"(=θ/4) from the state shown in FIG. 10, the image of the even portion has a luminance of about 50%, the image of one slope (surface C) in the concave having a inclination angle (θ'/2) which is (θ/4) has a luminance of about 100%, and the image of the other slope (surface D) has a luminance of about 0%.

In the surface inspection apparatus according to the above-described embodiments, although images are formed with a luminance corresponding to the incident angle for the measurement objective region, it is clearly possible to freely adjust the sensitivity for inspecting the concave by changing the diffusion (spread) angle of the reflected lights from the even portion in the measurement objective region, that is, the irradiation angular aperture, or by changing the object-side angular aperture θ. Therefore, in this embodiment, an angular aperture changing member 330 for changing the angular aperture of the aperture stop 310 is provided to freely change the object-side angular aperture θ. If an aperture diameter changing member 125 for changing the aperture diameter of the aperture stop 122 is also provided to move with each other, it is possible to very easily adjust the sensitivity.

In the surface inspection apparatus according to the embodiments, although the image pickup part 400 picks up images which was formed by the object-side telecentric optical system 300, while the processing part 520 collects the luminance data for every pixel (for each point in the measurement objective region), the luminance data are collected for example with 256 gradations.

The processing part 520 processes the collected luminance data for every pixel in the inclination direction of the object to be measured, thereby to determine the shape or the like of the measurement objective region. The way taken for processing luminance data will be explained as a case of the inclined measurement object 900 which has a measurement objective region with a shape similar to that of FIG. 10.

Figure 13A:
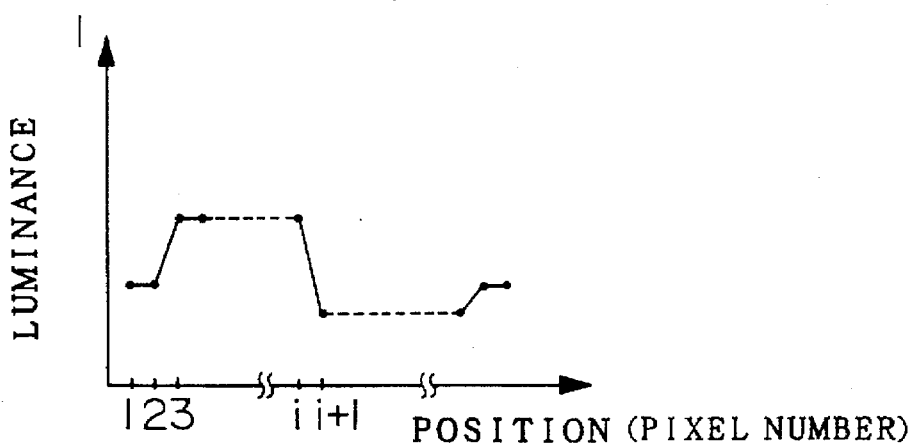
FIGS. 13A, 13B and 13C are explanation view of luminance data processing operation of the surface inspection apparatus according to the second embodiment of the present invention.
Figure 13B:
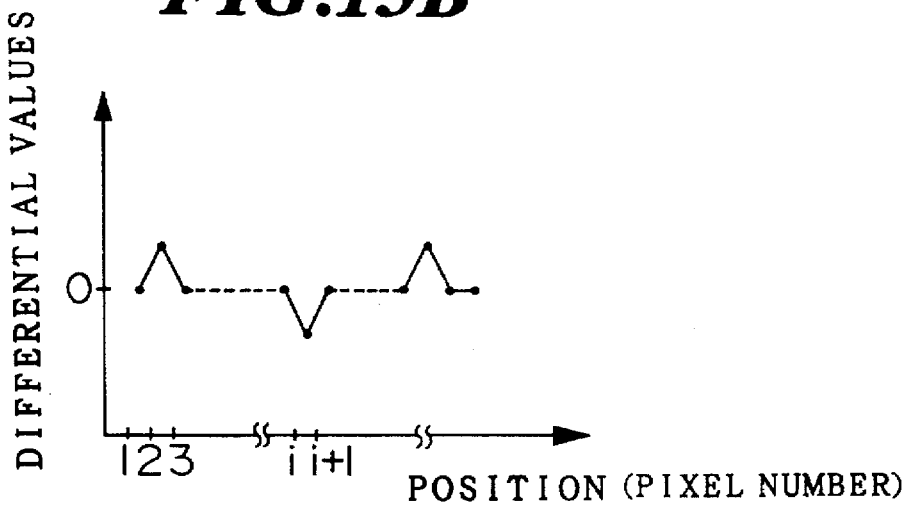
Figure 13C:
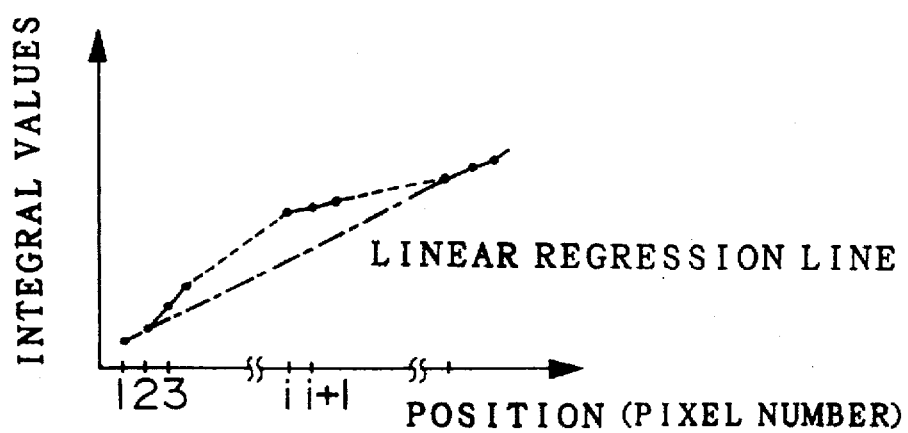
Figure 14:
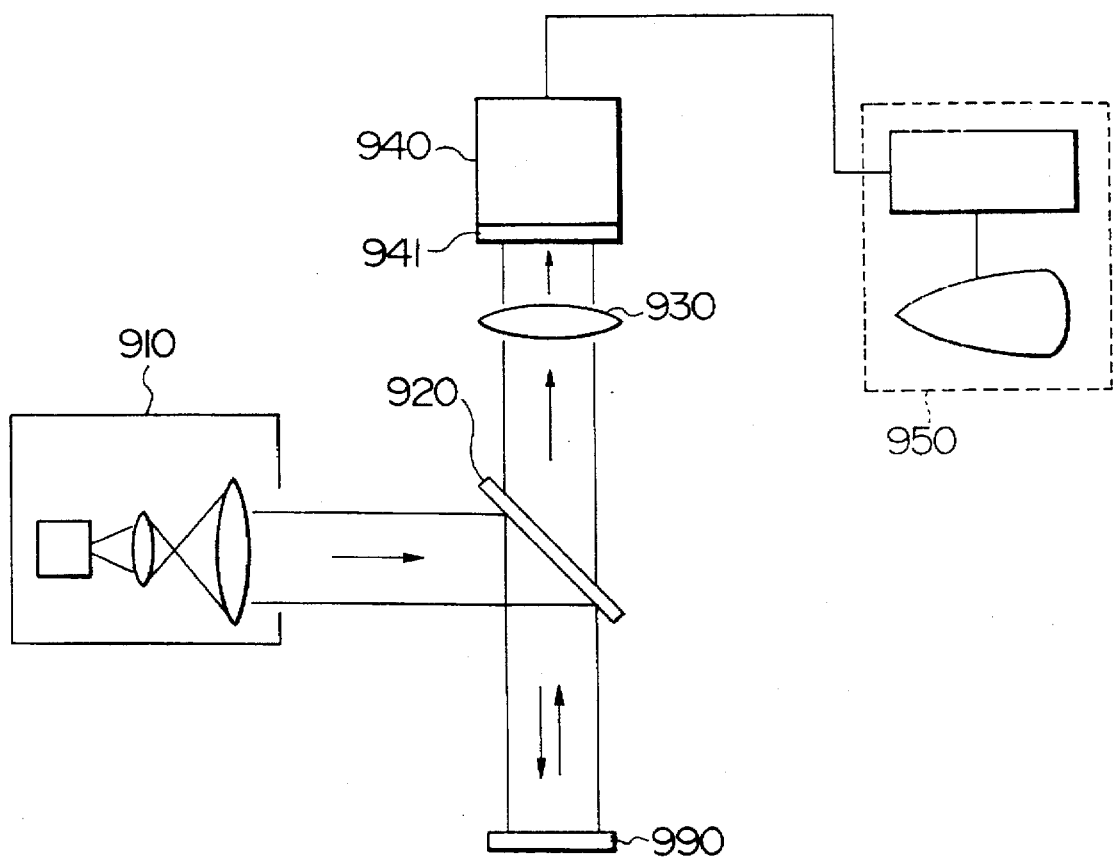
FIG. 14 is a schematic view showing the construction of a conventional surface inspection apparatus.

FIGS. 13A, 13B and 13C are schematic views for explaining a luminance data processing. By operating the difference between luminance data of adjacent pixels ($I_{i+1}-I_i$) on the basis of the luminance data of pixels arranged in an inclined direction (Refer to FIG. 13A), a linear differential of the luminance data distribution is obtained with respect to a line in the inclined direction, that is, a scanning line in the data processing, as shown in FIG. 13B. Since the data obtained by the linear differential reflect an inclination quantity of the measurement objective region, an inclination distribution along the scanning line can be determined from the results of the linear differential.

Then, the luminance data of the pixels at from the initial position, which is usually the end pixel, to a desired pixel are integrated, i.e., $I_1+ \ldots +I_i$, to obtain the integral data at respective positions, as shown in FIG. 13C.

Thereafter, the irregularity of the measurement objective region is determined on the basis of the difference between a regression curve obtained from the integral data and the integral data.

The results obtained from the difference between respective regression curves including a linear regression line and the integral data can be displayed with a predetermined gradation display, for example, 8 gradation display or 16 gradation display, so as to display only irregular portions corresponding to a desired frequency.

As described above, according to the embodiment, a desired specific irregular portion can be easily found from its luminance data. For example, in the case of a silicon-wafer, low order components such as undulation, bow or warp can be extracted from the difference between the integral data and the linear regression line. Further, irregular portions such as mounds, dimples and slipline can be extracted from the difference between the integral data and higher order regression curves such as those of third degree, fifth degree or seventh degree.

In the second embodiment, it is desirable to collect both luminance data obtained in the case of an inclination of the measurement objective region in one direction (X direction) and those obtained in the case of an inclination of the measurement objective region in the other direction (Y direction) crossing with the X direction.

In general, when a measurement objective region is inclined with respect to the reference plane, luminances of respective points are changed corresponding to the inclination thereof with respect to the reference plane. The surface inspection apparatus according to this embodiment is what enables determination of the presence or absence and the shape of the irregular portions by using the variation of luminances. In this case, however, it occurs some cases wherein the irregular portions (such as undulation or slip) having a crest and a valley extending along a single axis can not be exactly inspected only by inclining the measurement objective region around the single axis.

Therefore, the measurement objective region is inclined with respect to X and Y axes crossing with each other in the measurement objective region (preferably, with the same inclination angle), and the luminance data are collected in the respective inclined position, so as to determine the presence or absence and the shape of the irregular portions thereon by utilizing both the collected luminance data. In this way, it is possible to exactly catch the presence or absence and the shapes of the irregular potions having crests and valleys extending along the axis.

Preferably, in the processing part, a first luminance data of respective points in the objective region when the object to be measured is inclined at a predetermined angle in one direction with respect to an axis in a reference plane which is perpendicular to the incident direction of the illuminating light and a second luminance data of respective points in the objective region when the object to be measured is inclined at the same angle as the above in the other direction with respect to the axis are summed together, and about ½ of the maximum value of the summed value is used as a value for medium gradation and at least one of the first and second luminance data is used as a processing objective luminance data.

This will be explained with reference to FIGS. 12A and 12B. When the measurement objective region is inclined at an angle of θ"(=θ/4) toward the right side from the state shown in FIG. 10, the images of the flat surface portion, the left side slope portion, and the right side slope portion have luminances of 50%, 0%, and 100%, respectively. On the other hand, when the measurement objective region is inclined at an angle of θ"(=θ/4) toward the left side from the state shown in FIG. 10, the images of the flat surface portion, the left side slope portion, and the right side slope portion have luminances of 50%, 100%, and 0%, respectively. The luminance data obtained through such a manner are summed together, and about ½ of the maximum value of the summed value is used as a value for a medium gradation and at least one of the luminance data obtained from the states shown in FIGS. 12A and 12B is used as a processing objective luminance data for the processing part 520. By such a manner, the portion with a luminance of 50% (the flat portion) has the medium gradation. Because processing of the luminance data is carried out by using the flat portion as a standard, it is possible to process the luminance data easily. When the medium gradation is determined, preferably, the processing objective luminance data are processed so that the minimum to the maximum, of the luminance data which are the processing objective luminance data are arranged in predetermined gradations, for example, 256 gradations. Accordingly, the inspection sensitivity of irregular portions is further increased.

In order to collect respective luminance data with respect to X and Y axes which cross with each other in the measurement objective region, by inclining the measurement objective region with respect to the X and Y axes (preferably, inclining at approximately the same angle for these axes), to determine the presence or absence and the shape of the irregular portions thereon by utilizing both the collected luminance data, the following processing may be carried out. Preferably, the luminance data of the measurement objective region are collected when the measurement objective region is inclined at approximately the same angle in an opposite direction to each other with respect to the X and Y axes crossing with each other, more preferably, perpendicularly to each other, and it is preferable to use about ½ of the maximum value of the sum of the two luminance data with respect to the axes as a value for medium gradation.

Although the present invention has been explained according to the embodiments, it should also be understood that the present invention is not limited to the embodiments and that various changes and modifications maybe made to the invention without departing from the gist thereof.

For example, although a point light source has been formed by using a light source and an aperture in the second embodiment, the present invention can be applied to use a light source itself such as an LED itself as a point light source without an aperture.

In the case where the measurement object region has a camber with a predetermined curvature, it is also possible to adopt an inspection method in which the rear surface of the object 900 to be measured is sucked by vacuum to use the rear surface as a reference plane, or another method in which an aperture 112 or an aperture stop 122 is moved in close or moved away from the half mirror 113 or 123, to irradiate respective points on the measurement objective region with a light in the normal direction and to form an image of the reflected light through the object-side telecentric optical system 300. In the former case, a linear regression curve is determined, and irregular portions are determined by using the rear surface of the measurement object as the reference plane. On the contrary, in the latter case, a linear regression curve is determined, and irregular portions are determined by using the surface having a camber of the measurement object as the reference plane.

In the second embodiment, although the inclination angle θ" of the measurement objective region with respect to the reference plane is set equal to (θ/4), as well as the first embodiment, an inclination angle other than that can be also set to change the inspection sensitivity for concave portions or convex portions.

Further, in the embodiments, an object-side telecentric optical system 300 is used. However, telecentric optical systems can be provided both in the object side and in the image side. It is required that a telecentric optical system is used at least in the object side.

As described above, according to the surface inspection method of the present invention, it is possible to simply and precisely inspect the surface characteristics of a measurement objective region by the combination of a telecentric optical system and an illuminating optical system.

According to the surface inspection device of the present invention, because the illuminating light from the light source is reflected on the measurement objective region, and the reflected light forms an image through an object-side telecentric optical system or an image-object-side telecentric optical system, it is possible to suitably carry out the surface inspection method according to the invention and to inspect the shape or the state of the measurement objective region with a high accuracy.

Further, the surface inspection can be carried out with a sensitivity corresponding to the object-side angular aperture by additionally providing an angular aperture changing member for changing the aperture diameter of the aperture stop.

What is claimed is:

1. A surface inspection method for inspecting a surface condition of an objective region to be measured by irradiating the objective region with an illuminating light of an approximately parallel beam, comprising the steps of:

setting an object-side angular aperture such that whole reflecting light beams from a surface perpendicular to an incident direction of an illuminating light just enters into a light limiting member;

irradiating an objective region to be measured with an illuminating light in an oblique direction thereto;

forming an image of reflected light from the objective region by one system selected from the group consisting of an object-side telecentric optical system and an image object-side telecentric optical system, which has an optical axis coinciding with an incident direction of the illuminating light to the objective region, the formed image of reflected light having points with luminance corresponding to the incident angle of the illuminating light at respective points on the objective region;

picking up the formed image to collect luminance data of the respective points in the objective region; and processing the luminance data to recognize bright and dark portions and thereby determining the presence or absence of an irregular portion and a shape of the irregular portion, in the objective region.

2. A surface inspection method as claimed in claim 1, wherein in the step of processing the luminance data, a first luminance data of respective points in the objective region when the objective region to be measured is inclined at a predetermined angle in one direction with respect to an axis in a reference plane which is perpendicular to the incident direction of the illuminating light and a second luminance data of respective points in the objective region when the object to be measured is inclined at the same angle as the above in the other direction with respect to the axis are summed together, and about ½ of the maximum value of the summed value is used as a value for medium gradation and at least one of the first and second luminance data is used as a processing objective luminance data.

3. A surface inspection method as claimed in claim 2, wherein the illuminating light at respective points on the objective region has a predetermined certain irradiating angular aperture, and the object-side angular aperture is set to be substantially equal to the predetermined certain irradiating angular aperture.

4. A surface inspection method as claimed in claim 2, wherein the illuminating light at respective points on the objective region has a predetermined certain irradiating angular aperture, and the object-side angular aperture is set to be substantially equal to the predetermined certain irradiating angular aperture; and in the step of processing the luminance data, both a luminance data when the object to be measured is inclined with respect to one axis in a reference plane which is perpendicular to the incident direction of the illuminating light and a luminance data when the object to be measured is inclined with respect to another axis in the reference plane, which is perpendicular to the one axis, are used as processing objective luminance data, and these two processing objective luminance data are composite to determine the presence or absence of an irregular portion and a shape of the irregular portion, on the objective region to be measured.

5. A surface inspection method as claimed in claim 1, wherein in the step of processing the luminance data, both a luminance data when the objective region to be measured is inclined with respect to one axis in a reference plane which is perpendicular to the incident direction of the illuminating light and a luminance data when the objective region to be measured is inclined with respect to another axis in the reference plane, which is perpendicular to the one axis, are used as processing objective luminance data, and these two processing objective luminance data are composite to determine the presence or absence of an irregular portion and a shape of the irregular portion, on the objective region to be measured.

6. A surface inspection method as claimed in claim 5, wherein the illuminating light at respective points on the objective region has a predetermined certain irradiating angular aperture, and the object-side angular aperture is set to be substantially equal to the predetermined certain irradiating angular aperture.

7. A surface inspection method as claimed in claim 1, wherein the illuminating light at respective points on the objective region has a predetermined certain irradiating angular aperture.

8. A surface inspection method as claimed in claim 1, wherein the illuminating light at respective points on the objective region has a predetermined certain irradiating angular aperture, and the object-side angular aperture is set to be substantially equal to the predetermined certain irradiating angular aperture.

9. A surface inspection method for inspecting a surface condition of an objective region to be measured by irradiating the objective region with an illuminating light of an approximately parallel beam, comprising the steps of:

setting an object-side angular aperture such that whole reflecting light beams from a surface perpendicular to an incident direction of an illuminating light just enters into a light limiting member;

inclining an object to be measured and irradiating an objective region to be measured with an illuminating light in an oblique direction thereto;

forming an image of reflected light from the objective region by one system selected from the group consisting of an object-side telecentric optical system and an image object-side telecentric optical system, which has an optical axis coinciding with an incident direction of the illuminating light to the objective region, the formed image of reflected light having points with luminance corresponding to the incident angle of the illuminating light at respective points on the objective region;

picking up the formed image to collect luminance data of respective points in the objective region; and processing the luminance data to determine an inclination distribution of the objective region on the basis of linear differential results of the luminance data and to determine the presence or absence of an irregular portion and a shape of the irregular portion, in the objective region, on the basis of the difference between a regression curve obtained from an integral data of the luminance data and the integral data.

10. A surface inspection method as claimed in claim 9, wherein the illuminating light at respective points on the objective region has a predetermined certain irradiating angular aperture.

11. A surface inspection method as claimed in claim 9, wherein the illuminating light at respective points on the objective region has a predetermined certain irradiating angular aperture, and the object-side angular aperture is set to be substantially equal to the predetermined certain irradiating angular aperture.

12. A surface inspection apparatus for inspecting a surface condition of an objective region to be measured by irradiating the objective region, comprising:

a light limiting member for enabling a setting of an object-side angular aperture such that whole reflecting light beams from a surface perpendicular to an incident direction of an illuminating light just enters into the light limiting member;

a light irradiating member for irradiating the objective region with an illuminating light of a parallel beam thereto;

an angle setting member for inclining an object to be measured to irradiate the objective region to be measured with the illuminating light in an oblique direction thereto;

one system selected from the group consisting of an object-side telecentric optical system and an image-object-side telecentric optical system, for forming an image of reflected light from the objective region, which has an optical axis coinciding with an incident direction of the illuminating light to the objective region, the formed image of reflected light having points with luminance corresponding to the incident angle of the illuminating light at respective points on the objective region;

a pick-up part for picking up the formed image to collect luminance data of respective points in the objective region; and a processing part for processing the luminance data to recognize bright and dark portions and thereby determining the presence or absence of an irregular portion and a shape of the irregular portion, in the objective region.

13. A surface inspection apparatus as claimed in claim 12, further comprising an angular aperture changing member for changing the object-side angular aperture.

14. A surface inspection apparatus as claimed in claim 13, wherein the light irradiating member comprises a light source and an aperture stop, and the apparatus further comprises an aperture diameter changing member for changing an aperture diameter of the aperture stop correspondingly to a change of the object-side angular aperture.

15. A surface inspection apparatus as claimed in claim 12, wherein in the processing part, a first luminance data of respective points in the objective region when the object to be measured is inclined at a predetermined angle in one direction with respect to an axis in a reference plane which is perpendicular to the incident direction of the illuminating light and a second luminance data of respective points in the objective region when the object to be measured is inclined at the same angle as the above in the other direction with respect to the axis are summed together, and about ½ of the maximum value of the summed value is used as a value for medium gradation and at least one of the first and second luminance data is used as a processing objective luminance data.

16. A surface inspection apparatus as claimed in claim 12, wherein in the processing part, both a luminance data when the object to be measured is inclined with respect to one axis in a reference plane which is perpendicular to the incident direction of the illuminating light and a luminance data when the object to be measured is inclined with respect to another axis in the reference plane, which is perpendicular to the one axis, are used as processing objective luminance data, and these two processing objective luminance data are composited to determine the presence or absence of an irregular portion and a shape of the irregular portion, on the object to be measured.

17. A surface inspection apparatus as claimed in claim 12, wherein the illuminating light at respective points on the objective region has a predetermined certain irradiating angular aperture.

18. A surface inspection apparatus for inspecting a shape of an irregular potion in an objective region to be measured by irradiating the objective region, comprising:

a light limiting member for enabling a setting of an object-side angular aperture such that whole reflecting light beams from a surface perpendicular to an incident direction of an illuminating light just enters into the light limiting member;

a light irradiating member for irradiating the objective region with an illuminating light of a parallel beam;

an angle setting member for inclining an object to be measured to irradiate an objective region to be measured with the illuminating light in an oblique direction thereto;

one system selected from the group consisting of an object-side telecentric optical system and an image-object-side telecentric optical system, for forming an image of reflected light from the objective region with respective luminances corresponding to incident angles at respective points in the objective region, which has an optical axis coinciding with an incident direction of the illuminating light to the objective region, the formed image of reflected light having points with luminance corresponding to the incident angle of the illuminating light at respective points on the objective region;

a pick-up part for picking up the formed image to collect luminance data of respective points in the objective region; and a processing part for processing the luminance data to determine an inclination distribution of the objective region on the basis of linear differential results of the luminance data and to determine the presence or absence of an irregular portion and a shape of the irregular portion, in the objective region, on the basis of the difference between a regression curve obtained from an integral data of the luminance data and the integral data.

19. A surface inspection apparatus as claimed in claim 18, further comprising an angular aperture changing member for changing the object-side angular aperture.

20. A surface inspection apparatus as claimed in claim 18, wherein the illuminating light at respective points on the objective region has a predetermined certain irradiating angular aperture.

* * * * *